(12) United States Patent
Guild

(10) Patent No.: US 7,559,980 B2
(45) Date of Patent: Jul. 14, 2009

(54) ABSORBENT TRANSFER FOR PASSIVE SAMPLING BADGE

(75) Inventor: Lloyd V. Guild, McMurray, PA (US)

(73) Assignee: SKC, Inc., Eighty Four, PA (US)

( * ) Notice: Subject to any disclaimer, the term of this patent is extended or adjusted under 35 U.S.C. 154(b) by 394 days.

(21) Appl. No.: 11/613,761

(22) Filed: Dec. 20, 2006

(65) Prior Publication Data

US 2007/0163436 A1 Jul. 19, 2007

Related U.S. Application Data

(60) Provisional application No. 60/760,023, filed on Jan. 18, 2006.

(51) Int. Cl.
*B01D 53/04* (2006.01)
*G01N 1/22* (2006.01)

(52) U.S. Cl. .............................. 96/147; 96/151; 96/413; 73/863.23; 422/88

(58) Field of Classification Search ................... 96/147, 96/151, 413; 95/90, 148; 73/19.02, 23.35, 73/23.42, 863.21, 863.23; 422/88, 89; 436/178
See application file for complete search history.

(56) References Cited

U.S. PATENT DOCUMENTS

| | | | | |
|---|---|---|---|---|
| 1,839,350 | A | * | 1/1932 | Slagel .......................... 96/118 |
| 2,031,164 | A | * | 2/1936 | Johnson ........................ 96/147 |
| 3,950,980 | A |   | 4/1976 | Braun et al. |
| 4,040,805 | A | * | 8/1977 | Nelms et al. ...................... 96/4 |
| 4,205,043 | A |   | 5/1980 | Esch et al. |
| 4,256,694 | A | * | 3/1981 | McAllister et al. ............. 422/58 |
| 4,258,000 | A |   | 3/1981 | Obermayer |
| 4,389,372 | A | * | 6/1983 | Lalin ............................ 422/88 |
| 4,528,160 | A | * | 7/1985 | Eckstein et al. ................. 422/6 |
| 4,680,165 | A |   | 7/1987 | Vo-Dinh |
| 5,517,866 | A | * | 5/1996 | Manning et al. .......... 73/863.21 |
| 5,571,948 | A | * | 11/1996 | Kaplan et al. ............... 73/31.05 |
| 6,050,150 | A |   | 4/2000 | Underhill |
| 6,063,041 | A | * | 5/2000 | Flament et al. .............. 600/573 |
| 6,607,581 | B2 |   | 8/2003 | Smith et al. |

\* cited by examiner

*Primary Examiner*—Frank M Lawrence
(74) *Attorney, Agent, or Firm*—Beck & Thomas P.C.

(57) ABSTRACT

A passive air sampler or badge suitable for wearing includes a vial adaptor to facilitate transferring granular or particulate adsorbent to and from it directly into a specially designed vial sized to accommodate a standard amount for use in a desorption tube for chromatographic or other analysis of the materials desorbed.

19 Claims, 3 Drawing Sheets

ABSORBENT TRANSFER FOR PASSIVE SAMPLING BADGE

CROSS REFERENCE TO RELATED APPLICATION

This application claims the benefit of U.S. Provisional Application No. 60/760,023, filed Jan. 18, 2006.

TECHNICAL FIELD

This invention relates to sampling of air contaminants and particularly to passive air samplers of the type worn as a badge. It is especially applicable to methods of obtaining samples of volatile organic compounds ("VOC") and the transfer of adsorbent materials into and out of the air samplers.

BACKGROUND OF THE INVENTION

Passive air samplers are devices worn by personnel working in environments in which it is desirable to monitor exposure to various contaminants in the air, usually organic vapors. Such devices are known as badges because they can be clipped or otherwise temporarily fastened to the user's clothing and worn there for a recorded period of time, usually the entire shift or other working period in the atmosphere in question. The badges are called passive samplers because they have no pump or other accessory to assure the flow of air through them. Sampling relies on simple exposure to the atmosphere, not a measured or predetermined flow volume, but sampling badges may be distinguished from indicating badges, in that indicating badges may change color in the presence of a specific contaminant. In a sampling badge, extraction of the contaminants such as volatile organics from the air is accomplished by adsorbents in the badge. They are usually granular, made of porous polymer or sometimes activated carbon, and may or may not be treated to enhance the ability to adsorb a particular organic chemical.

Where the identification and quantification of the adsorbed material is to be performed by gas chromatography, the used or impregnated adsorbent is subjected to thermal desorption and/or flushed with an inert gas such as nitrogen for sending to the gas chromatograph. For use in the gas chromatograph, the inert gas containing the desorbed contaminant is passed through a standard thermal desorption sampler tube which contains a second adsorbent. The material is then analyzed by the standard gas chromatographic techniques, which involve passing a further inert gas through the thermal desorption sampler tube.

Patents illustrating passive air sampling badges include Nelms et al U.S. Pat. No. 4,040,805 and Esch et al U.S. Pat. No. 4,205,043. See also Obermayer U.S. Pat. No. 4,258,000, Braun et al U.S. Pat. No. 3,950,980, Vo-Dinh U.S. Pat. No. 4,680,165 and Underhill et al U.S. Pat. No. 6,050,150. None of these describes the features of the present invention.

In the conventional process of interest in the present review, the contaminant is first picked up on an adsorbent in the badge, the contaminant is desorbed from the badge adsorbent and picked up on the chromatograph adsorbent, and then desorbed again for the actual analysis. This process has been criticized for having too many steps, which are time-consuming and may be a source of error, and for excessive adsorbing and desorbing, which can also lead to error. Many of the disadvantages of the conventional procedure have been overcome by the introduction of the device and method disclosed in Smith and Hall U.S. Pat. No. 6,607,581, the entirety of which is incorporated herein by reference. The Smith and Hall concept is, briefly, that a measured amount of adsorbent is confined in a funnel-shaped container in the badge, and after its assigned exposure, the impregnated adsorbent is poured from the funnel-shaped container into a container that can be used as a desorption tube for chromatographic analysis. Although this concept is efficient and convenient, like the more conventional procedure it does not facilitate the re-use of either the adsorbent or the transfer container. It may be said that the present invention is an improvement on the device and method of U.S. Pat. No. 6,607,581.

SUMMARY OF THE INVENTION

I have invented a device and method for the passive sampling of air which involves only one desorption step. It is simple to use and less subject to error than systems used in the past. My passive sampler is designed to permit the convenient reuse of both the badge and the sorbent material. My badge is designed to operate in a manner similar to that of the Smith and Hall '581 patent, but can be filled with adsorbent directly from a vial designed for the purpose. The vial contains a measured amount of sorbent and has been purged of volatile materials. The vial attaches to an adaptor on the neck of the sorbent container in the badge for transfer of the sorbent; the sorbent can then conveniently be transferred directly by draining or otherwise to a chromatographic desorption tube for desorption and analysis of the impregnated sorbent. After use—that is, after the sorbent has been desorbed in the gas chromatograph, it can be replaced in the vial, which is sealed accordingly. The sorbent-containing vial can then be used to refill the badge, which in the meantime has been sealed immediately after pouring the sorbent into the vial. My invention includes a passive air sampler comprising particulate adsorbent and a container therefor, the container including an opening for draining to empty the particulate adsorbent by gravity from the container, having a shape to facilitate the draining, and particularly including a vial adaptor for facilitating the attachment of a vial to the badge air sampler. It also includes such a container in an empty state in combination with a vial containing adsorbent in an amount useful for desorption and analysis, normally by gas chromatography.

DETAILED DESCRIPTION OF THE INVENTION

Figure 1:
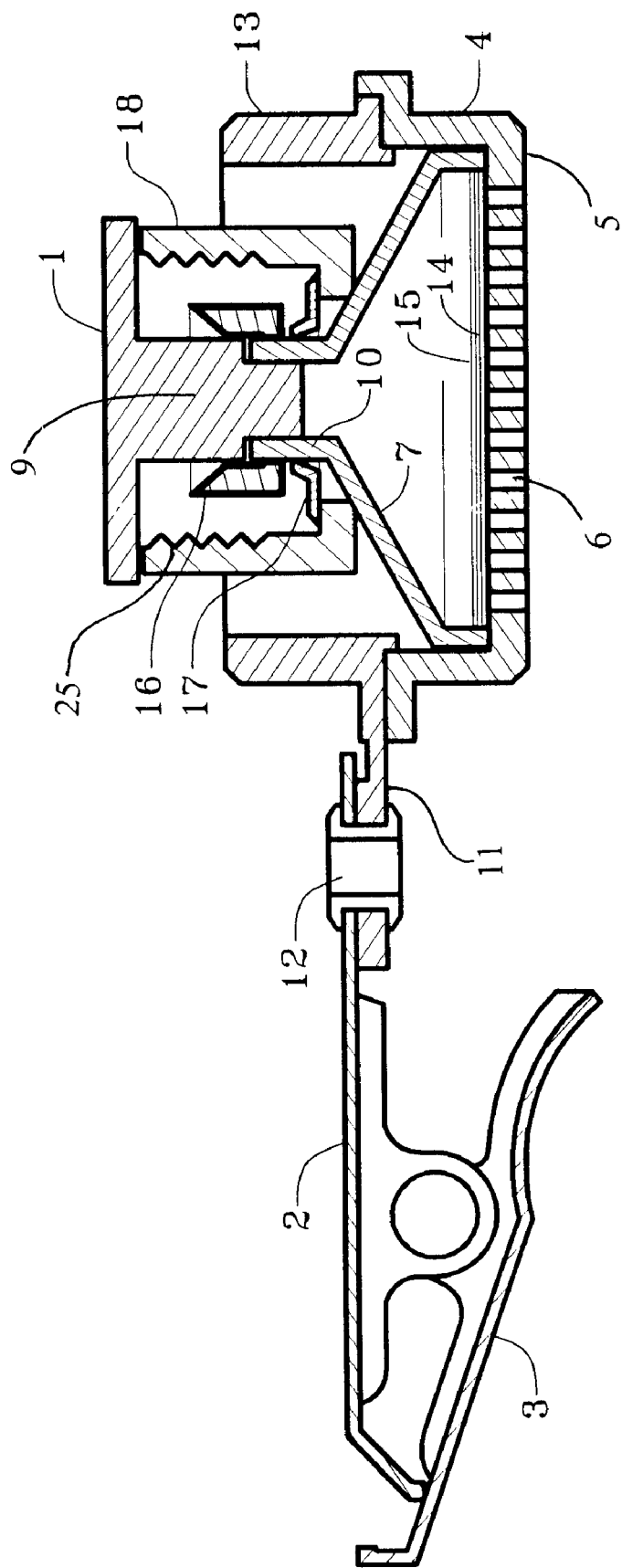
FIG. 1 is a side sectional view of my badge.

Referring now to FIG. 1, a passive sampler of the invention is in the form of a badge having a badge base 4, a badge body 13, a back 1 and a fastener 2 for holding the badge to the user's clothing. The fastener 2 may be a clip having a spring-actuated clip handle 3 and may be mounted on a swivel 12 through attachment 11. The front 5 of the sampler has a plurality of apertures 6 for admitting the atmosphere to its interior. Back 1 has a plug end 9 for fitting into ferrule 16 and substantially cylindrical neck 10 of adsorbent container 7. Plug end 9 forms a snug fit in neck 10 in order to assure that volatiles and contaminants to be adsorbed in the adsorbent do not escape through neck 10; ferrule 16 reinforces neck 10 and plug end 9.

Adsorbent container 7 holds adsorbent material such as particulate or granular (which is frequently regenerable) activated carbon, not shown. Other useful particulate or granular adsorbents are known by the trademarks TENAX, ANASORB 747, and ANASORB CMS. Any synthetic or natural material capable of adsorbing one or more target contaminants or volatile organic compounds ("VOC's") may be used. Preferably container 7 is filled or substantially filled with such adsorbent material. The adsorbent material is preferably held compactly in the container 7 yet loosely enough to permit air to penetrate to its interior in order to pick up contaminants. While plug end 9 of back 1 is normally snugly fitted into neck 10 of container 7, it is manually removable along with back 1 to permit the passage of particulate adsorbent into and out of container 7. Ferrule 16 has a conically shaped inlet surface to help guide plug end 9 into neck 10 of container 7. Around neck 10 is a retainer ring 17, which also helps to position substantially cylindrical vial adaptor 18 having internal threads 25.

Figure 2:
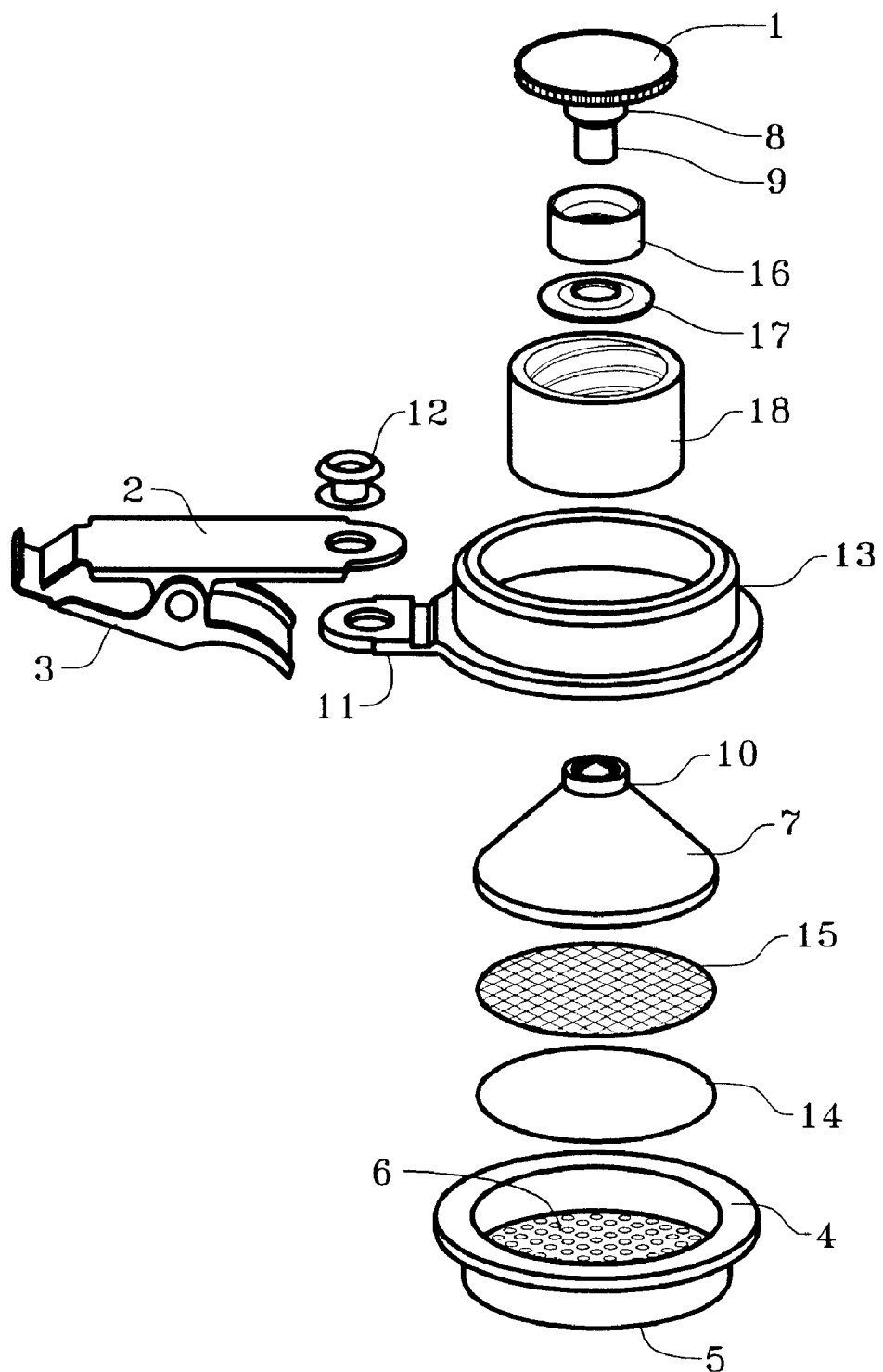
FIG. 2 is a vertically exploded view of the parts of my badge.

In FIG. 2, the parts of the badge (passive air sampler) are dissembled to illustrate their relationship. Badge base 4 includes front 5 and apertures 6 as shown in FIG. 1. Optional membrane 14 is placed next to front 5 to reject water in the air. For this purpose a water-selective membrane made by Celgard, Inc. and designated CELGARD (a trademark) may be used. Gaseous water vapor is not undesirable, but water droplets, however small, are generally not wanted in the sampler. Next after the membrane 14 is a screen 15, designed and positioned to separate the adsorbent from the membrane 14, and to form a conducting surface around the adsorbent to minimize electrostatic attraction of the adsorbent to the interior of the unit. The adsorbent container 7, preferably conical in shape, is next placed in the badge base 4. Badge body 13 is then placed over and around container 7 (see FIG. 1), and fastener 2 is attached by inserting swivel 12 through the fastener and attachment 11. Adsorbent container 7 is filled with adsorbent by pouring the granular or particulate adsorbent through neck 10 of container 7. This procedure is partly illustrated in FIG. 3. Vial adaptor 18, retainer ring 17, and ferrule 16 are positioned as shown in FIG. 1. Plug end 9 of back 1 is lowered onto the badge body 13 so that it will project into neck 10 of adsorbent container 7. Preferably the amount of granular or particulate adsorbent in container 7 is such that the plug end 9 touches it lightly. The volume of adsorbent is preferably an amount which will fill a standard thermal desorption tube; accordingly the internal volume of adsorbent container 7 is preferably no greater than that of a commonly used thermal desorption tube, i.e. about three and one-half inches long and about one-quarter inch diameter; of course other sizes may be used to meet variations in standards and required sample sizes. The fully assembled badge is now ready for use. New and refilled badges will be protected from ambient air by a further protective covering of any suitable kind, not shown, to prevent contamination before actual use. After removing the protective covering, the user may attach the badge to his or her clothing using the fastener 2. Usually the badge will be attached to the collar or otherwise relatively near the head in order to sample the air in the vicinity of that which is actually breathed by the user.

Figure 3:
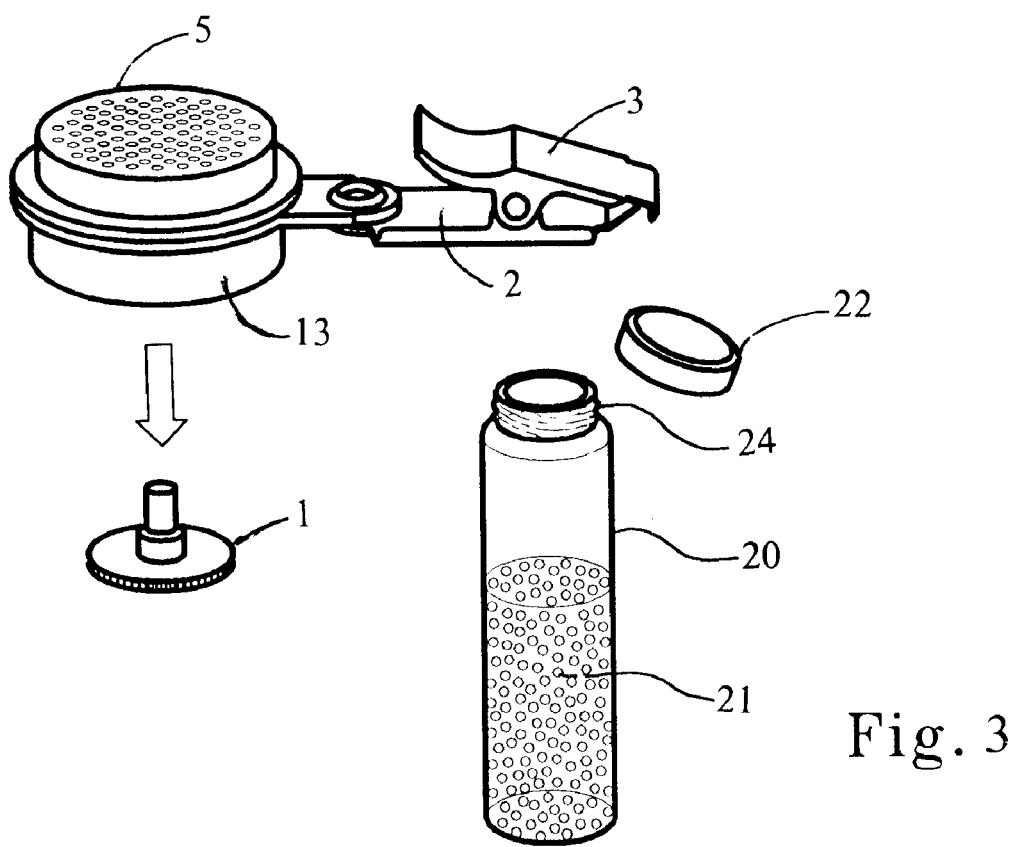
FIG. 3 shows the preparation of the valve and badge for transfer of the adsorbent from the vial to the badge.

In FIG. 3, a cap 22 has been removed from substantially cylindrical vial 20, containing fresh particulate adsorbent 21. As indicated above, the amount of adsorbent 21 in vial 20 is usually a standard amount for use in a desorption tube for chromatographic analysis, and may fill the vial 20. The empty badge has been inverted from its orientation in FIG. 1, and back 1 has been removed. Vial 20 is then inserted and screwed into adaptor 18 using threads 24 and complementary threads 25 on vial adaptor 18 (see FIG. 1). The assembly of the badge and vial is again inverted so that the adsorbent 21 will pass by gravity into adsorbent container 7. The vial is removed while still inverted, and back 1 is replaced to achieve the configuration of FIG. 1 with the addition of adsorbent in container 7, making sure that plug 9 is inserted into neck 10 of container 7. The badge is now ready for use with fresh adsorbent. If use at a later time or in a different location is contemplated, a cover should be placed over front 5 to close apertures 6 to the atmosphere until the new work environment or other location to be sampled is reached. The initial time and location of exposure will preferably be noted in a log, and the cover should be replaced at the end of the work shift or other significant time.

Figure 4:
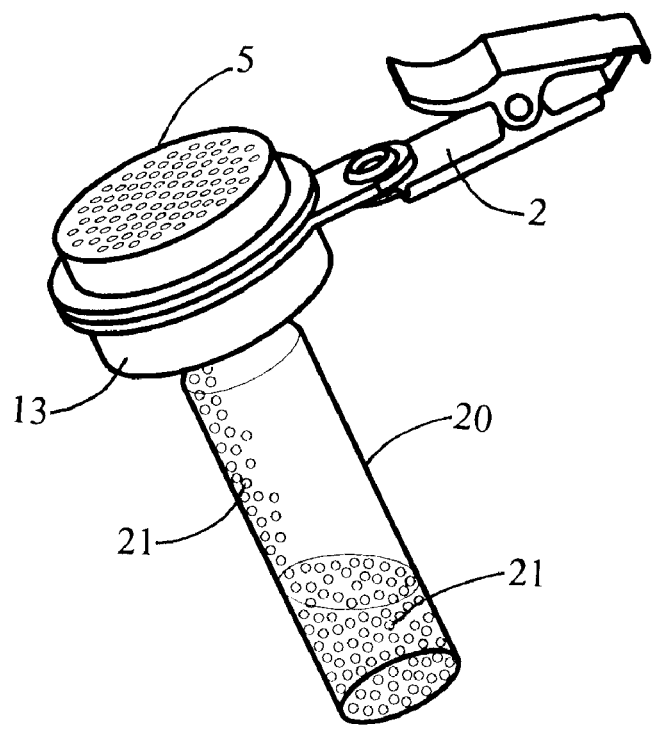
In FIG. 4, adsorbent is shown being drained into the valve after use.

FIG. 4 shows the orientation of the badge as the exposed adsorbent is removed from the badge. While the badge is oriented more or less as in FIG. 1, the back 1, including plug end 9, is removed and an empty vial 20 is screwed into adaptor 18 on threads 24 and 25. The assembly is then inverted, as shown in FIG. 4, resulting in a draining of the adsorbent 21 from container 7 into vial 20. The vial 20 is then removed, cap 22 is replaced on vial 20, and vial 20 is taken for desorption of adsorbent 21 and analysis of the desorbed materials.

The illustrated adsorbent container 7 having neck 10 is similar to that shown in U.S. Pat. No. 6,607,581. The angle of the cone (funnel) is not critical, but when the container is inverted, at least one inclined surface should be in a position to assist the draining of the adsorbent by gravity. Where a funnel or conical shape is used, the slope of the draining surface is preferably between 10 and 80°, more preferably between 15 and 45°, and most preferably between 20 and 35°. The illustrated angle is 27° and has been found quite satisfactory for any of the standard granular adsorbents. I do not intend to be limited to adsorbent container shapes and designs which require inversion to drain the adsorbent. Any combination of shape and orientation of the adsorbent outlet which will facilitate the draining of adsorbent may be used. Likewise, the basic shape and construction of the container lends itself to variation. Persons skilled in the art will recognize that the use of a vial adaptor together with a complementary vial facilitates the transfer of adsorbent both into and out of the badge, and enables re-use of the adsorbent after it is desorbed for analysis. Used particulate adsorbent is drained from the desorption tube into an empty vial 20; the vial 20 is closed with a cap 22 and kept for filling a badge again as described in connection with FIG. 3. Several iterations of the use and re-use may be performed. Persons skilled in the art will also recognize that vial adaptor 18 may be constructed with external threads instead of internal threads 25, where a vial is built with complimentary internal threads.

Thus my invention includes a passive air sampler comprising a container for particulate adsorbent, an opening in the container for receiving the particulate adsorbent by gravity and draining the particulate adsorbent by gravity from the container and having a shape to facilitate the draining, a removable plug for securing the adsorbent in the container, and a vial adaptor attached to the opening, the vial adaptor being of a size and shape to permit placement of a vial containing particulate adsorbent on the adaptor for transferring particulate adsorbent by gravity therefrom to the container and from the container to the vial.

My invention further includes a device for transferring particulate adsorbent from a vial to a passive air sampler, comprising (a) a passive air sampler including a vial adaptor having threads for receiving a threaded vial, and (b) a vial including particulate adsorbent therein, said vial having been opened and attached to said vial adaptor by vial threads complementary to said adaptor threads for transferring said particulate adsorbent from said vial to said passive air sampler.

Further, my invention includes a method of sampling contaminants in a gas comprising (a) placing the open end of a vial containing a known amount of particulate adsorbent on the vial adaptor of a passive air sampler as described, (b) by gravity, transferring the particulate adsorbent from the vial to the container of the passive air sampler, (c) exposing the particulate adsorbent in the passive air sampler to the gas while the particulate adsorbent is in the passive air sampler, whereby contaminants in the gas are adsorbed by the particulate adsorbent, (d) placing the open end of an empty vial on the vial adaptor, (e) by gravity, draining the particulate adsorbent from the container of the passive air sampler to the vial, and (f) transferring the particulate adsorbent from the vial to a desorption tube for chromatographic or other analysis of the contaminants.

In addition, my invention includes Method of obtaining and analyzing samples of contaminants in air in a workplace comprising (a) transferring a known amount of absorbent from a vial to a passive air sampler badge through an opening in said air sampler badge (b) sealing said opening (c) attaching said air sampler badge to a person's clothing for wearing through a measured period of time in said workplace (d) removing said air sampler badge from said clothing (e) unsealing said opening and draining said adsorbent into a vial (f) closing said vial (g) transferring said adsorbent from said vial into a desorption tube for analysis of desorbed contaminants (h) desorbing said contaminants for analysis, (i) transferring the desorbed adsorbent from said desorption tube to a vial and capping said vial (j) reusing said adsorbent by repeating steps (a) to (i).

The invention claimed is:

1. A passive air sampler comprising a container for particulate adsorbent, an opening in said container for receiving said particulate adsorbent by gravity and draining said particulate adsorbent by gravity from said container and having a shape to facilitate said draining, a removable plug for securing said adsorbent in said container, and a vial adaptor attached to said opening, said vial adaptor being of a size and shape to permit placement of a vial containing particulate adsorbent on said adaptor for transferring particulate adsorbent by gravity therefrom to said container and from said container to said vial.

2. A passive air sampler of claim 1 wherein said vial and said vial adaptor have complementary threads for placement of said vial on said vial adaptor.

3. A passive air sampler of claim 1 wherein said vial and said vial adaptor are substantially cylindrical.

4. A passive air sampler of claim 1 including a fastener for attaching said air sampler to a person's clothing.

5. A passive air sampler of claim 1 wherein said opening in said container is in the form of a substantially cylindrical neck and said removable plug forms a snug fit therein for securing said adsorbent in said container.

6. A passive air sampler of claim 1 including particulate adsorbent in said container.

7. A passive air sampler of claim 1 wherein said container has apertures to facilitate exposure of said adsorbent to the atmosphere outside of said air sampler.

8. A method of sampling contaminants in a gas comprising (a) placing the open end of a vial containing a known amount of particulate adsorbent on a vial adaptor of a passive air sampler, (b) by gravity, transferring said particulate adsorbent from said vial to the container of said passive air sampler, (c) exposing the particulate adsorbent in the passive air sampler to said gas while said particulate adsorbent is in said passive air sampler, whereby contaminants in said gas are adsorbed by said particulate adsorbent, (d) placing the open end of an empty vial on said vial adaptor, (e) by gravity, draining said particulate adsorbent from said container of said passive air sampler to said vial, and (f) transferring said particulate adsorbent from said vial to a desorption tube for chromatographic or other analysis of said contaminants.

9. Method of claim 8 followed by introducing particulate adsorbent to said vial.

10. Method of claim 9 followed by at least one iteration of claim 8 using said vial containing said particulate adsorbent obtained by the method of claim 9.

11. Method of claim 8 wherein said particulate adsorbent is previously unused adsorbent.

12. Method of claim 9 wherein said particulate adsorbent is desorbed adsorbent obtained on completion of step (f) of the method of claim 8.

13. Method of claim 8 wherein, between step (b) and step (c), the adsorbent is protected from exposure to the atmosphere.

14. A device for transferring particulate adsorbent from a vial to a passive air sampler, comprising (a) a passive air sampler including a vial adaptor having threads for receiving a threaded vial, and (b) a vial including particulate adsorbent therein, said vial having been opened and attached to said vial adaptor by vial threads complementary to said adaptor threads for transferring said particulate adsorbent from said vial to said passive air sampler.

15. A device of claim 14 wherein said passive air sampler includes a funnel-shaped adsorbent container.

16. A device of claim 14 wherein the threads on said vial adaptor are internal threads and the vial threads are external threads.

17. Method of obtaining and analyzing samples of contaminants in air in a workplace comprising (a) transferring a known amount of absorbent from a vial to a passive air sampler badge through an opening in said air sampler badge (b) sealing said opening (c) attaching said air sampler badge to a person's clothing for wearing through a measured period of time in said workplace (d) removing said air sampler badge from said clothing (e) unsealing said opening and draining said adsorbent into a vial (f) closing said vial (g) transferring said adsorbent from said vial into a desorption tube for analysis of desorbed contaminants (h) desorbing said contaminants for analysis, (i) transferring the desorbed adsorbent from said desorption tube to a vial and capping said vial (j) reusing said adsorbent by repeating steps (a) to (i).

18. Method of claim 17 wherein steps (a) and (e) are facilitated by complementary threads on said air sampler badge and said vial.

19. Method of claim 17 wherein the threads on said badge are in a substantially cylindrical vial adaptor surrounding the neck of a substantially funnel-shaped container in said badge.

* * * * *

UNITED STATES PATENT AND TRADEMARK OFFICE
CERTIFICATE OF CORRECTION

PATENT NO. : 7,559,980 B2 Page 1 of 1
APPLICATION NO. : 11/613761
DATED : July 14, 2009
INVENTOR(S) : Lloyd V. Guild It is certified that error appears in the above-identified patent and that said Letters Patent is hereby corrected as shown below:

Title page, Item (54) Title: cancel "ABSORBENT TRANSFER FOR PASSIVE" and insert --ADSORBENT TRANSFER FOR PASSIVE--

Column 1, Line 1 cancel "ABSORBENT TRANSFER FOR PASSIVE" and insert --ADSORBENT TRANSFER FOR PASSIVE--

Column 5, Line 21 cancel "amount of absorbent" and insert --amount of adsorbent--

Signed and Sealed this

Twenty-sixth Day of January, 2010

David J. Kappos
*Director of the United States Patent and Trademark Office*